United States Patent [19]

Rosenberg et al.

[11] Patent Number: 5,713,954
[45] Date of Patent: Feb. 3, 1998

[54] EXTRA CARDIAC VENTRICULAR ASSIST DEVICE

[75] Inventors: Meir Rosenberg, Newton; Robert T. V. Kung, Andover, both of Mass.

[73] Assignee: Abiomed R&D, Inc., Danvers, Mass.

[21] Appl. No.: 490,080

[22] Filed: Jun. 13, 1995

[51] Int. Cl.$^6$ .................................................. A61M 1/12
[52] U.S. Cl. ................................ 623/3; 600/17; 601/153
[58] Field of Search .................................... 600/16, 17, 31, 600/37; 601/153, 151, 152; 623/3

[56] References Cited

U.S. PATENT DOCUMENTS

| | | | |
|---|---|---|---|
| 3,464,322 | 9/1969 | Pequignot | 623/2 X |
| 3,587,567 | 6/1971 | Schiff | 128/24.5 |
| 3,613,672 | 10/1971 | Schiff | 601/153 X |
| 4,536,893 | 8/1985 | Parravicini | 623/3 |
| 4,690,134 | 9/1987 | Snyders | 128/64 |
| 4,957,477 | 9/1990 | Lundbäck | 600/16 |
| 5,098,369 | 3/1992 | Heilman et al. | 600/16 |
| 5,119,804 | 6/1992 | Anstadt | 601/153 |
| 5,131,905 | 7/1992 | Grooters | 600/16 |
| 5,534,024 | 7/1996 | Rogers et al. | 623/1 |

FOREIGN PATENT DOCUMENTS

| | | | |
|---|---|---|---|
| 0370931 | 5/1990 | European Pat. Off. | 601/151 |
| 1734767 | 5/1992 | U.S.S.R. | 600/16 |

OTHER PUBLICATIONS

Anstadt, G.L., Blakemore, W.S., Baue, A.E., "A New Instrument for Prolonged Mechanical Cardiac Massage", Circulation 31 and 32 (suppl II, II–43–II–44, 1965.

Anstadt, M.P., Anstadt, G.L., Lowe, J.E., "Direct Mechanical Ventricular Actuation: A Review", Resuscitation, 21:7–23, 1991.

Anstadt, M.P., Stonnington, M.J., Tedder, M., Crain, B.J., Brothers, M.F., Hilleren, D.J., Rahija, R.J. Menius, J.A. Lowe, J.E., "Pulsatile Reperfusion After Cardiac Arrest Improves Neurologic Outcome", Annals of Surg 214 (4):478–490, 1991.

Bencini, A., Parola, P.L., "The 'Pneumo Massage' of the Heart", Surgery 39:375–384, 1956.

Carpentier, A. and Chachque, J.C., "Mycardial Substitution with a Stimulated Skeletal Muscle: First Successful Clinical Case", Lancet, 1:1267, 1985.

Carpentier, A. Chachque, J.C., Acar C., et al, "Dynamic Cardiomyoplasty At Seven Years", J. Thorac and Cardiovasc Surg 106(1):42,54, 1993.

Primary Examiner—David H. Willse
Attorney, Agent, or Firm—Lahive & Cockfield, LLP

[57] ABSTRACT

An artificial implantable heart assist system with an artificial myocardium employs a number of flexible, non-distensible tubes with the walls along their long axes connected in series to form a cuff. The tubes are sealed for purposes of inflation and deflation with either hydraulic fluid or pneumatic fluid. The cuff is placed around the natural heart. The inflation of the tubular segments provides that they have a circular cross-section, while in the deflated, or collapsed position without being fluid filled, they are essentially flat sheets. The difference in the perimeter length of the cuff in the plane of the tube short axis, arising from the fact that, inflated, each tube has a length along its perimeter equal to the diameter of the inflated tube, while deflated it has a length equal to the perimeter of the tube divided by two, provides for a contractile force. An energy converter is provided in the system for shuttling fluid between a compliant reservoir and the cuff in phase with the systolic and diastolic phase of the natural heart. This system is powered by an internal implanted battery, which can be recharged transcutaneously from an external power source.

13 Claims, 12 Drawing Sheets

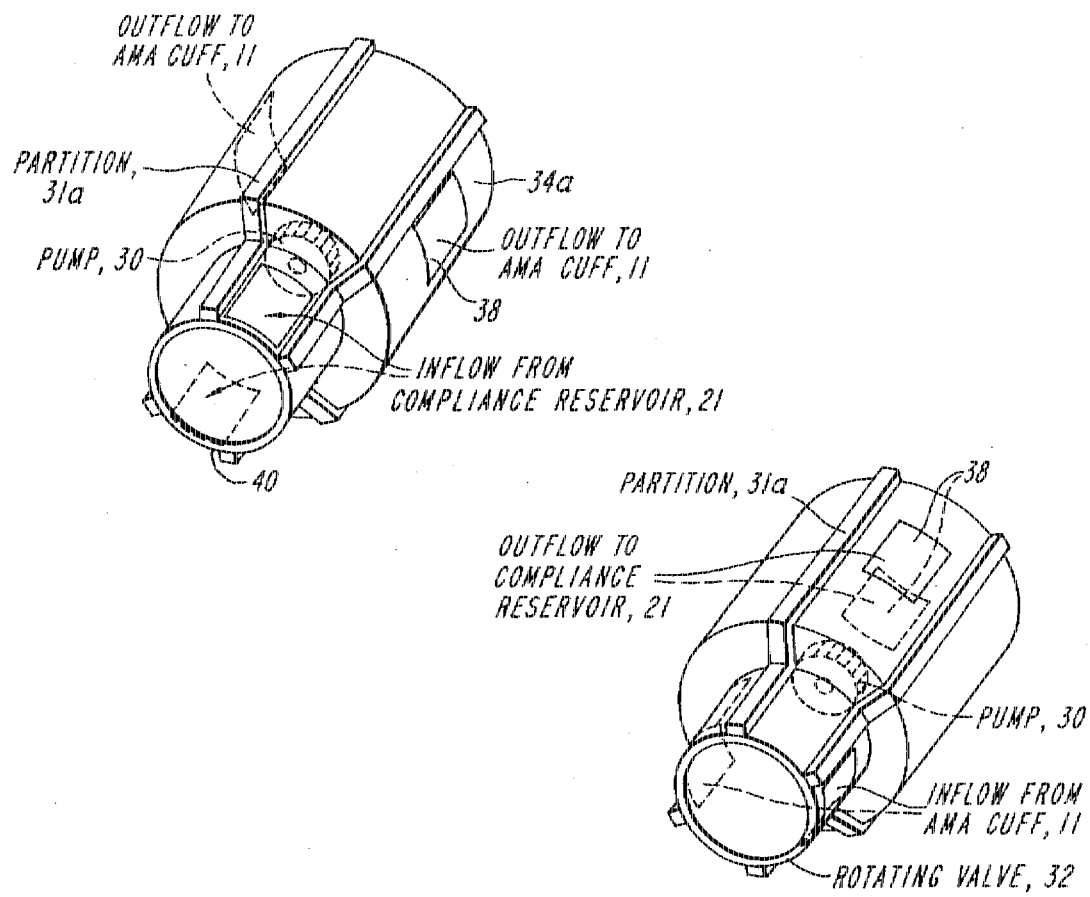
FIG. 11A
FIG. 11B
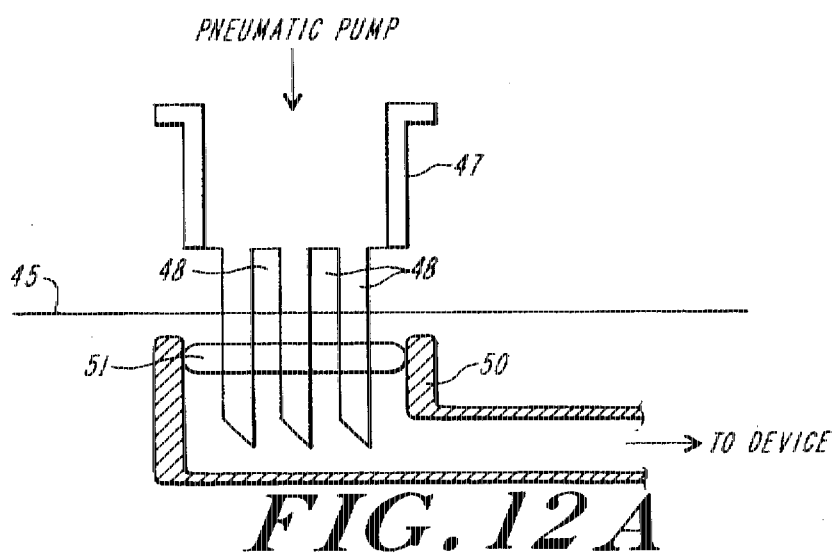
FIG. 12A

EXTRA CARDIAC VENTRICULAR ASSIST DEVICE

FIELD OF THE INVENTION

This invention relates in general to cardiac assist systems and more particularly to an artificial myocardium for wrapping around one or both ventricles of a natural heart generating controlled contractile forces to provide auxiliary pumping action to these ventricles in phase with the contractions of the natural heart.

BACKGROUND OF THE INVENTION

A number of cardiac assist systems employing a variety of pumping approaches for assisting the pumping action of a failing natural heart have been developed. These systems include those suitable for partial to full support of the natural heart, short term (a few days) to long term (years), continuous pumping to various degrees of pulsability, and blood contacting versus non-blood contacting. Table 1 lists a number of presently developed devices with pertinent operating characteristics.

TABLE 1

| Device | Level of Support | Pulsatility | Duration | Blood Contacting | Comment |
|---|---|---|---|---|---|
| IABP | Partial <20% | Y | Days to Months | Y | Counterpulsation provides LV unloading |
| Biopump | Full | N | Days | Y | Limited to short duration due to thrombotic potential |
| Thoractec | Full | Y | Months | Y | Sac-type actuation |
| Novacor | Full | Y | Months | Y | Sac-type pump with electric actuation |
| Hemopump | Partial 50-75% | N | Days | Y | Axial flow pump |
| Heart Mate | Full | Y | Months | Y | Pusher-Plate pneumatic and electric |
| Aortic Patch | Partial | Y | Months | Y | Counterpulsation |
| BVS 5000 | Full | Y | Weeks | Y | Designed for temporary support |
| Anstadt | Full | Y | Days | N | Cardiac resuscitation |
| Cardio-myoplasty | Partial <20% | Y | Years | N | Requires muscle training |

Some of these systems are implantable within the thoracic cavity, while others are inserted in appropriate blood vessels by the use of catheters, and others are external devices. Another approach which has been employed is to use housings of rigid construction for enveloping, at least partially, the ventricular region of a myocardium. The inner surface of the housing has a distensible elastic membrane adjacent to the myocardial wall. Pumping fluids are fed to the chambers defined by the housing and the membrane to effect pressure on the myocardial wall. In some instances the outer portion of the housing is formed of a flexible, but non-distensible member with an elastic distensible inner membrane. In general these approaches employ filling of a compartment or number of compartments each characterized by the elastic inner wall and inelastic outer wall, thereby compressing the myocardium of the ventricle to aid pumping. Assist devices of this type are described in U.S. Pat. Nos. 3,587,567; 4,536,893; 4,690,134 and 5,131,905. Similar approaches have employed a concave, gel filled compression pad activated by a plate on its outer surface (U.S. Pat. No. 5,098,369), and an entirely passive approach, such as described in U.S. Pat. No. 4,957,477, which involves heart assist provided by a fluid filled jacket encasing at least the heart ventricles to provide a compliant, completely passive support.

A major consideration in the design of cardiac support systems is the risk of thromboembolism. This risk is most associated with use of artificial blood contacting surfaces. A variety of approaches have been employed to reduce or eliminate this problem. One approach has been the employment of smooth surfaces to eliminate potential sites for thrombi and emboli generation as well as textured surfaces to promote cell growth and stabilization of biologic surfaces. One problem affecting thromboembolism risk in heart assists arises from the use of prosthetic, biologic or mechanical pericardial valves. This risk can be some what lowered by the use of anticoagulation therapy. However, the use requires careful manipulation of the coagulation system to maintain an acceptable balance between bleeding and thromboembolic complications. The textured surface approach employs textured polyurethane surfaces and porcine valves to promote pseudo-intima formation with a stable cellular lining. While thromboembolic rates resulting from these measures are acceptable as temporary measures, improvements, particularly for implantable devices are highly desirable.

A second problem associated with implanted cardiac assist devices is the problem of infection, particularly where the implanted device has large areas of material in contact with blood and tissue. More recently clinical protocols have improved and even the drive line and vent tubes associated with implants that require some percutaneous attachments have been manageable. However, for a ventricular assist device, quality of life considerations require that vent lines and drive lines which cross the skin barrier be eliminated thereby avoiding the encumbrance to patient activities.

A third problem area in ventricular assist devices is the calcification of these devices. This is particularly so for long term implant situations which may last five years or more. Here again the criticality of this factor is reduced for devices which do not involve direct blood contact.

Another approach employed in ventricular assist has been the development of non-pulsatile pumps. However, once again, the blood is exposed to the surfaces of the pump, particularly the bearing and seal area.

Unlike an entirely artificial heart, in which failure of the system leads to death, a ventricular assist device augments the impaired heart and stoppages should not result in death, unless the heart is in complete failure. However, for most present ventricular assist device systems, stoppage of even a few minutes results in formation of blood clots in the device, rendering any restart of the system a very risky undertaking.

It is therefore an object of the present invention to produce a ventricular assist device system employing an artificial myocardium placed around the natural heart (extra cardiac assist). This design, then, does not contact the bloodstream eliminating many of the problems discussed above.

It is another object of this invention to provide a ventricular assist device which mimics the action of the natural heart while avoiding the compressive action of the direct mechanical ventricular actuation systems on the epicardium.

It is a further object of this invention to provide an artificial myocardium in which the external fluid being pumped is a fraction of the blood volume pumped by the action of the artificial myocardium.

It is yet another object of this invention to provide a ventricular assist device which is compact, requires relatively low energy input and does not require percutaneous components.

SUMMARY OF THE INVENTION

Broadly speaking, in the present invention an artificial myocardium is constructed of an extremely pliant, non-distensible and thin material which can be wrapped around the ventricles of a natural, but diseased heart. This artificial myocardium mimics the contraction-relaxation characteristics of the natural myocardium and provides sufficient contractility, when actuated, to at least equal the contractility of a healthy natural myocardium. In this arrangement all of the direct blood contact is with the interior surfaces of the natural heart and surrounding blood vessel system. The device is hydraulically actuated in timed relationship to the contractions of the natural heart.

Using this system, the natural heart is left in place and the assist system supplies the reinforcing contractile forces required for satisfactory ventricular ejection.

A key concept for this artificial myocardium system is achieved by the realization of a controllable, artificial myocardium employing a cuff formed of a series of closed tubes connected along their axially extending walls. With sufficient hardware to hydraulically (or pneumatically) inflate and deflate these tubes, a controlled contraction is produced as a result of the geometric relationship between the length of these series of tubes in deflated condition and the length of the series of tubes when they are fluidically filled in the inflated condition. If the cuff is formed of a series of "n" tubes, each of diameter "d" when inflated, connected in series, the total perimeter length of this cuff when deflated is given by $n(\pi d/2)$. However, when these tubes are filled with fluid, they have a circular cross-section such that the length of the cuff is the sum of the diameters in the individual tubes or nd. Thus the ratio of the change in perimeter length between the collapsed and the filled state is $\pi/2$. If this cuff is wrapped around the natural heart, it will, when pressurized, shorten and squeeze the heart by producing a "diastolic" to "systolic" length change of 36%. Typical sarcomere length changes are approximately 20%.

Suitable hardware, including a hydraulic pump, a compliant reservoir and rotary mechanical valve, together with appropriate actuating electronics can all be implanted in the patient's body. If the power source is an internal battery, then power may be transcutaneously transmitted into the body to recharge this battery.

DESCRIPTION OF THE DRAWING

In the drawing:

FIG. 11A is a cross-sectional view of an energy converter and valve structure in one position for use in the artificial myocardium of this invention;

FIG. 11B is a cross sectional view of the same structure as FIG. 11A but with the valving in a different position for pumping from the hydraulic cuff to the hydraulic reservoir;

FIG. 12A is a cross-sectional view across the skin interface of a subdermal port for emergency access and manual pumping;

DESCRIPTION OF PREFERRED EMBODIMENTS

Figure 1A:
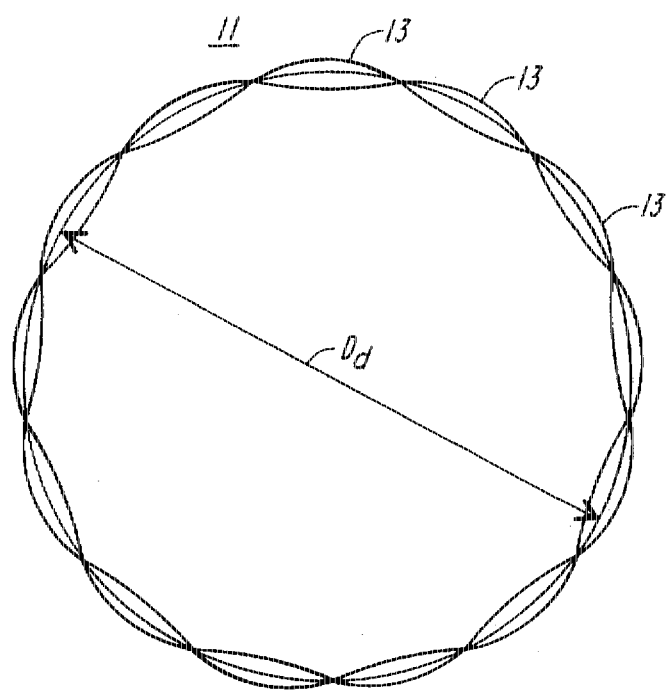
FIG. 1A and 1B are diagrammatic illustrations of the tube construction of an artificial myocardium in accordance with the principles of this invention.
Figure 1B:
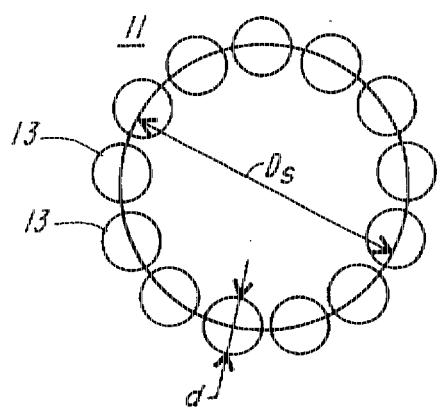

FIG. 1A and FIG. 1B illustrate diagrammatically the operation of the artificial myocardium. The artificial myocardium 11 is formed of a series of tubes planed together in series to form, in this instance a complete circle, which in FIG. 1A has a diameter $D_d$. In FIG. 1B the feature of the tubes is filled hydraulic fluid producing a circular cross-section, shortening the total perimeter of the circular cuff to a circle having a diameter $D_S$. Referring to FIG. 1B, if the diameter of the tube with the circular cross-section is d, then the diameter of the circular cuff is approximately equal to nd/π, where n equals the total number of tubes. On the other hand, when the tubes are no longer filled with hydraulic fluid and are collapsed then the diameter $D_d$ is approximately equal to $$\frac{n(\pi d/2)}{\pi}.$$

These expressions follow from the consideration that the series of n tubes in the inflated condition, as illustrated in FIG. 1B form a circle with the number of tubes times diameter of each of the individual tubes. On the other hand in the collapsed condition each one of the tubes has a length equal to its perimeter divided by 2. Since the perimeter is πd then the length of each collapsed tube is πd/2 and the diameter of the cuff in this condition is the sum of the length of the collapsed tubes over π.

When this cuff is placed around a natural heart and the filling and emptying of the tubes is in phase with the systole and diastole of the natural heart, then the shortening of the cuff forces the surrounded ventricle to decrease its diameter thereby causing the ventricle to eject blood. The ejection fraction of this artificial myocardium is independent of the number of tubes or the heart dimensions. The ejection fraction is a function of only the hydraulic pressure. When the hydraulic pressure is large enough to inflate the tubes to cylinders, the ejection fraction is, $$E_f = \frac{D_d^2 - D_s^2}{(D_d - 2t)^2},$$

where $$D_s = \frac{nd}{\pi}, D_d = \frac{(nd)}{2}, t = \text{heart muscle thickness}.$$

Figure 2:
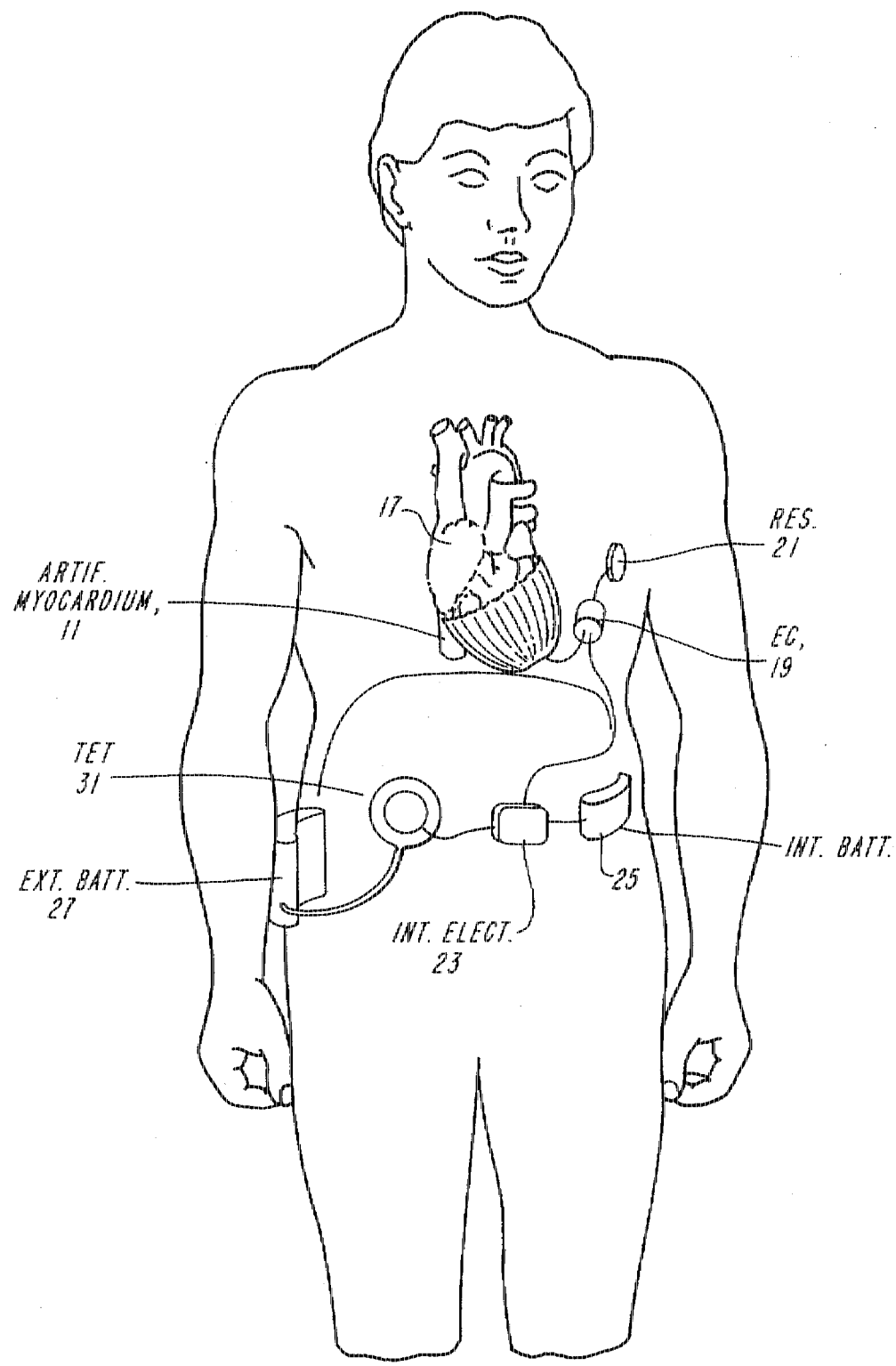
FIG. 2 is a generally diagrammatic illustration of the anatomical placement of the cardiac assist system of this invention in the human body.

FIG. 2 illustrates an artificial myocardial assist system located in the human body. In the illustrated system the artificial myocardium 11 is shown as a cuff placed around the ventricles of the natural heart 17. The hydraulic fluid is pressurized by energy converter 19 either in the direction of the cuff 11 or of a compliant hydraulic reservoir 21. The energy converter 19 is electrically controlled by virtue of internal electric circuit 23 which is powered by an internal battery 25. The internal electrical circuit 23 is also coupled to external battery 27 via a transcutaneous electrical terminal (TET) 31. The energy converter 19 consists of a hydraulic pump coupled to a brushless electric motor to shuttle fluid between the artificial myocardium 11 and the compliant reservoir 21. Flow switching is accomplished by a rotary mechanical valve incorporated into the energy converter, which in turn is synchronized by a control signal generated by detection of the R wave from the ECG signal in the natural heart. Continuous adjustment of the hydraulic pump output allows the level of cardiac assist to be varied on a beat-by-beat basis.

Figure 3A:
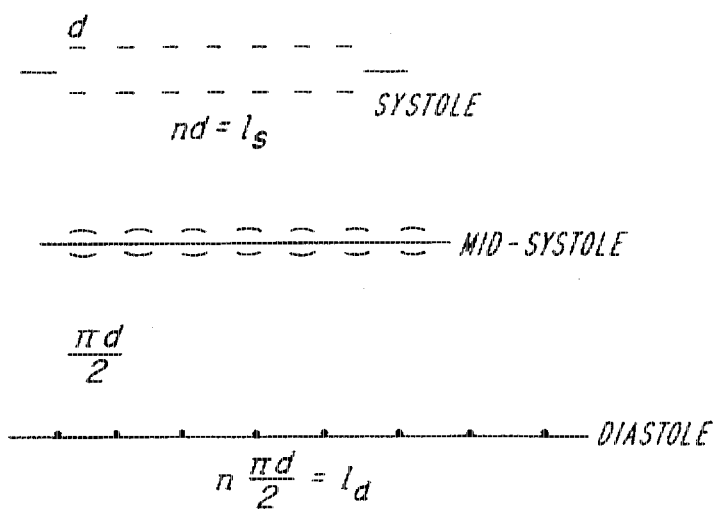
FIG. 3A is an illustration in diagrammatic form of the perimeter length of the artificial cuff at various stages of the natural heart contractions.
Figure 3B:
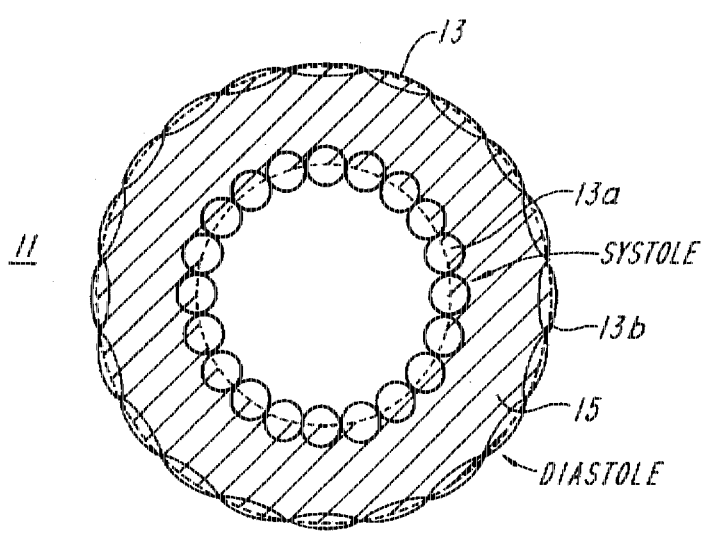
FIG. 3B is an illustration of a cross-sectional view of the systolic and diastolic shapes of the artificial myocardium.

FIG. 3A is a graphical illustration of the length of the perimeter of the artificial myocardium during systole, mid systole and diastole. FIG. 3B is an illustration in cross section view of the systolic and diastolic shapes of the artificial myocardium in a cylindrical geometry. The outer ring illustrates the cylindrical tubes in collapsed form, while the inner ring illustrates those same tubes when they are filled with hydraulic fluid during the systole. The natural heart pumps blood primarily through circumferential contraction. Most of the diastolic to systolic volume change is derived primarily from the 20% change in the circumference component and to a lesser extent the 9% change in the axial length. As can be seen in FIG. 3A and FIG. 3B, the volumetric change of the myocardium is 36% from the relaxed (diastole) position to the fully contracted (systole) position. In the cross-sectional view, and assuming that the artificial myocardium were a completely cylindrical cuff, there is a 60% change in the area between these states in the artificial myocardium, equivalent to a 60% ejection fraction of a healthy heart. Although the description is based on a cylindrical geometry, with interconnecting tapered tubes, the artificial myocardium will match the conical shape of the heart when appropriate taper angle is selected for the tubes.

With this hydraulic design, the natural heart having a typical myocardium thickness, a heart base diameter of 80 mm and an axial ventricular length from apex to base of 50 mm, a left ventricular wrap of the artificial myocardium results in a stroke volume of 83 cc. These values are the same as that which would be expected from a normally operating left ventricle.

One very important factor in the operation of the artificial myocardium is that the hydraulic pressure required for contraction against a given ventricular pressure is directly proportional to the number of tubes n forming this artificial myocardium. From energy conservation principles, the hydraulic flow in this artificial myocardium varies inversely with the number of tubes. For example, with typical natural heart dimensions, and a hydraulic stroke volume of 24 cc, a pressure of 760 mm Hg produces a left ventricular stroke volume of 95 cc at a mean aortic pressure of 90 mm Hg. Importantly, the hydraulic flows required are much less than the generated blood flow. In this example, the hydraulic flow is approximately 25% of the blood flow produced. These smaller hydraulic flows result in lower hydraulic losses and higher efficiencies. This, taken together with the smaller dimensions for the energy converter and the compliance chamber is very advantageous for an implanted device.

The output of a single energy converter can simultaneously generate different contractile forces for left and right ventricle assist by varying the number of tubes which are wrapped around the left and right ventricles while maintaining an equal drive pressure. If the artificial myocardium on the right side has M times the number of tubes as that on the left side, the contractile pressures on the right side will be M times lower. With this arrangement, the artificial myocardium may be tailored to match differing afterloads from the two ventricles. A good design parameter for considerations for efficiency and tube dynamics would be to operate at a contraction of 22%, which is very close to the contraction value of a natural healthy myocardium. It is believed that with this contraction level, the low mechanical stresses on the artificial myocardium may well result in an operation life of five years, a high reliability for the artificial myocardium.

In the artificial myocardium assist system of this embodiment the contribution from the artificial myocardium is additive to the natural heart with a timing cycle synchronized with the ECG, so that the control algorithm can adjust the hydraulic flow on a beat-by-beat basis to achieve the desired ejection fraction. Thus, if the natural myocardium was completely healthy, minimal pumping would be required by the hydraulic pump. On the other hand, if the natural heart had very little myocardial contractility, then the artificial myocardium would provide almost the entire contracting force.

With this design of the artificial ventricles there is no blood contact with the artificial surfaces of the cardiac assist system, thereby avoiding the principal concerns of the thromboembolism risk. Another important safety consideration, is that if the artificial myocardium system were to stop, the natural forces on the hydraulic fluid will cause it to empty from the artificial myocardium and flow into the compliant reservoir. The only effect of these conditions on the cardiovascular system would be those caused by the collapsed flexible wrap on the myocardium. A subdermal port could be provided to allow emergency actuation of the artificial myocardium with a pneumatic pump placed external to the patient's body. Another consideration is that the control algorithm of the artificial myocardium assist system can be arranged to provide contractions at a fixed predetermined rate if there should be a ventricular fibrillation or tachycardia of the natural heart.

Because the design provides for no contact between the blood and the components of the artificial myocardium assist system, the biocomparability factors are limited to those which relate to the interface between tissues and these components. In this embodiment, the tissue contacting material of the artificial myocardium may be a polyetherurethane, Angioflex ®, manufactured by ABIOMED, Inc. of Danvers, Mass.

Figure 4A:
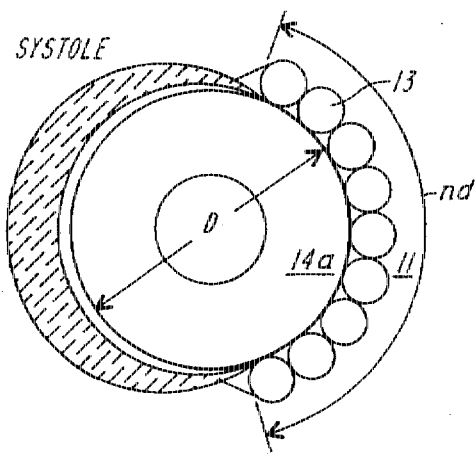
FIG. 4A is a diagrammatic view of a partial wraparound of the left ventricle by the artificial myocardium in the systolic state and FIG. 4B is a diagrammatic view of a partial wraparound of the left ventricle by the artificial myocardium in the diastolic state.
Figure 4B:
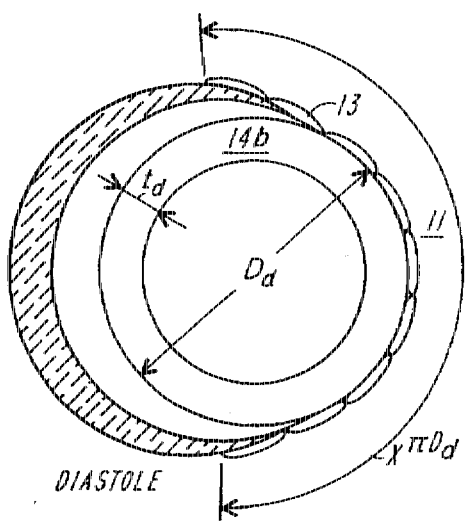

FIGS. 4A and 4B illustrate an example of a partial wrap around the heart for left ventricular support. The full wrap can be used for biventricular support. FIGS. 4A and 4B show the systolic and diastolic positions of the artificial myocardium under this condition. Each of the n tubes are attached at their outer wall to two neighboring tubes except for the two ends. Each tube, when inflated, has a diameter d, resulting in a wrap length of nd. Conversely, when the tubes are deflated the wrap length is $$\frac{n\pi d}{2}.$$

Figure 5:
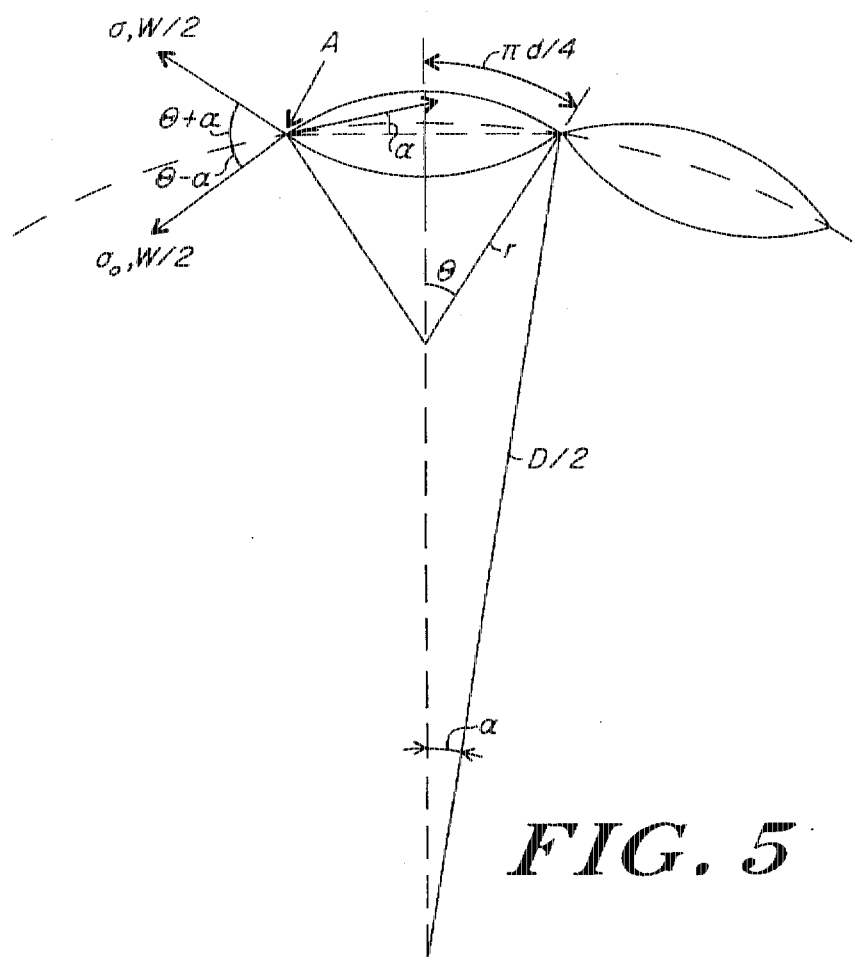
FIG. 5 is a diagrammatic illustration of the geometric relationship of the partially inflated tubes and the encircled heart represented by a radius of D/2.

As illustrated in FIG. 5, when the tubes are partially inflated the length of the wrap is given by $$L = nd \frac{\pi \sin\theta}{2\theta},$$

where θ is the angle representative of the curvature of the wall of the partially inflated tube and is defined as $$\theta = \frac{\pi d}{4r}.$$

where r is the radius of the arc of each half of the tube wall when inflated.

Although the ventricle is conical in shape and accordingly the artificial myocardium is conformed to that shape, for simplicity the representation in FIGS. 4A and 4B is of a cylindrical shape. In FIG. 3B the effects of both tube inflation and stroke volume are shown. The systolic contracted shape 13a of the artificial ventricle is plotted concentrically inside the diastolic distended shape 13b. The shaded annulus portion 15 of FIG. 3B represents the stroke volume change due to contraction, while the dotted circle enclosed portion of the inflated tubes represents displacement volume change. For the artificial myocardium this displacement volume has a minor contribution to the stroke volume.

The volume may be expressed as $$S_v = \frac{\pi}{4} D_d^2 \left[ 1 - \left( 1 - \chi + \chi \frac{\sin\theta}{\theta} \right)^2 \right] l + \frac{1}{2} V_H$$

where l is the perimeter length of the cuff, where $D_d$ is, as shown, the diastolic diameter of the ventricle and x is the fraction of the ventricle being wrapped. $V_H$ represents the actual displacement due to the effects of tube inflation in addition to the stroke volume derived from the contraction. If values are substituted in this equation, assuming a typical natural heart diameter of approximately 8 cm, a length approximately 5 cm and a left side partial wrap of x=½, the contractile change from the uninflated to fully inflated tubes results in a stroke volume of approximately 83 cc. $V_H$ is assumed to be zero. Similarly for a full wrap, the stroke volume would be approximately 150 cc, equivalent to the sum of left and right side stroke volumes.

The ejection fraction achievable using such an assist device may be estimated. The diastolic ventricular volume is given by $$V_d = \frac{\pi}{4} (D_d - 2t_d)^2 l,$$

where $t_d$ is the ventricular wall thickness. Since the ejection fraction is defined as the stroke volume divided by the diastolic ventricular volume, it is given by $$EF = S_v / \frac{\pi}{4} (D_d - 2t_d)^2 l.$$

Thus, the maximum ejection fraction obtainable for a typical wall thickness of 1 cm and a $D_d$ equal to 8 cm is 59%, a number which is consistent with the ejection fraction for a normal healthy heart.

Figure 6A:
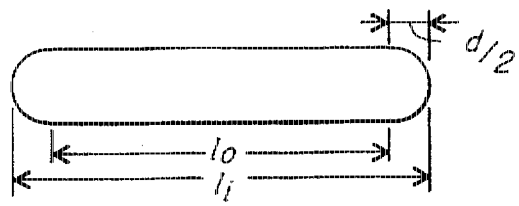
FIGS. 6A, 6B and 6C illustrate factors involved in altering the length of the individual tubes when inflated or deflated, to achieve specific shrink ratios.

FIG. 6A describes a section of a tube having an inflated diameter d and an inflated length l. The tube ends are formed to hemispheres in the inflated position, the hemisphere radius being d/2.

The following relation can be written:

$$l_i = l_o + d \tag{1}$$

where:

$l_i$ is the inflated length of the tube $l_o$ is the straight part of the tube d is the inflated diameter of the tube.

Figure 6B:
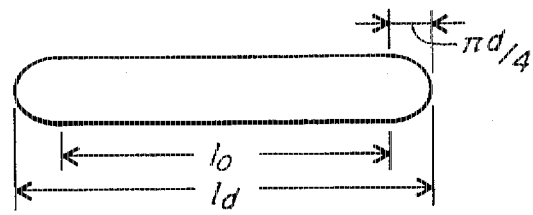

FIG. 6B describes the tube when it is deflated. The flattened diameter of the tube is πd/2 and its flattened length is:

$$l_d = l_o + \pi d/2 \tag{2}$$

where:

$l_d$ is the deflated length of the tube.

The shrink ratio, defined as the change in linear dimensions relative to the original linear dimension $l_d$, is:

$$R = \frac{\left[ l_0 + \frac{\pi d}{2} \right] - [l_0 + d]}{l_0 + \frac{\pi d}{2}} = \frac{d\left[ \frac{\pi}{2} - 1 \right]}{l_0 + \frac{\pi d}{2}} = \frac{\pi - 2}{2\frac{l_0}{d} + \pi} \tag{3}$$

Where:

R=relative change in linear dimensions.

As can be seen from the equation, the ratio R is only a function of the ratio between the diameter d and the length $l_o$. It can also be shown that this ratio does not change if a number of these tubes are connected in series provided $l_o/d$ remains unchanged.

Example: If the required longitudinal shrinkage is 12%, the ratio lo/d can be calculated, using equation (3) to be:

$$0.12 = \frac{\pi - 2}{\frac{2l_o + \pi}{d}} \quad (4)$$

$$l_o/d = 3.18$$

Figure 6C:
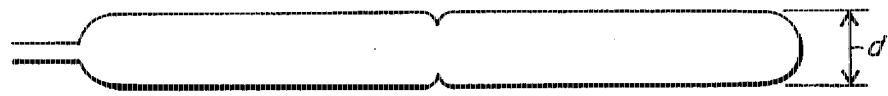

To achieve a contraction of 12% longitudinally, the tube length $l_o$ should be 3.18 times the diameter d. In a particular case, where the tube diameter is 10 mm, the overall tube length will be 41.8 mm. This length is about half of the required length and therefore, two of these tubes will be connected in series to achieve this goal. The series connection can be done by making two wraps of half length, or, making the individual tubes with a shape as described in FIG. 6C.

As discussed earlier the contractile action of the artificial myocardium results from the inflation of the series of tubes that are physically attached to each other. The inflation of these tubes can be accomplished either pneumatically or hydraulically. For a permanently implantable device, the hydraulic approach is more practical. With a pneumatic system, even in the absence of leakage losses, gas permeation across flexing membranes is unavoidable. This effect is not probable in a hydraulic system with a proper choice of working fluids. In addition, the hydraulic system is safer in the event of rupture failure since high pressure cannot be maintained in the event of a leak. In the case of a pneumatic system, a severe leak could result in cardiac compression. In the situation where the artificial myocardium is being employed as an assist device, the natural myocardium can generate some tension, and the artificial myocardium need only generate sufficient tension to boost the intraventricular pressure. Accordingly, the differential pressure, Prequired of the artificial myocardium may be only 20–30 mm Hg, boosting the ventricular pressure from, for example, 60 to 80–90 mm Hg. The ratio of hydraulic pressure $P_H$ to the load pressure P is expressed by $$\frac{P_H}{P} = \frac{n \tan \theta}{2\pi \cos \alpha} + \frac{1}{2} (1 - \tan \theta \tan \alpha).$$

$\alpha$ is the half angle subtended by each tube centered to the ventricular axis.

Accordingly, the pump pressure $P_H$ is related to three parameters. First it is directly proportional to load pressure. Thus higher load pressures requires higher drive pressures. Secondly, as the number of tubes, n increases, the drive pressure required for a given boost of intraventricular pressure increases. This is accompanied by a concomitant decrease in the fluid flow of volume per stroke required of the hydraulic pump system. Third, the hydraulic pressure required increases as the tubes are progressively inflated from being fully deflated to fully circular.

Figure 7:
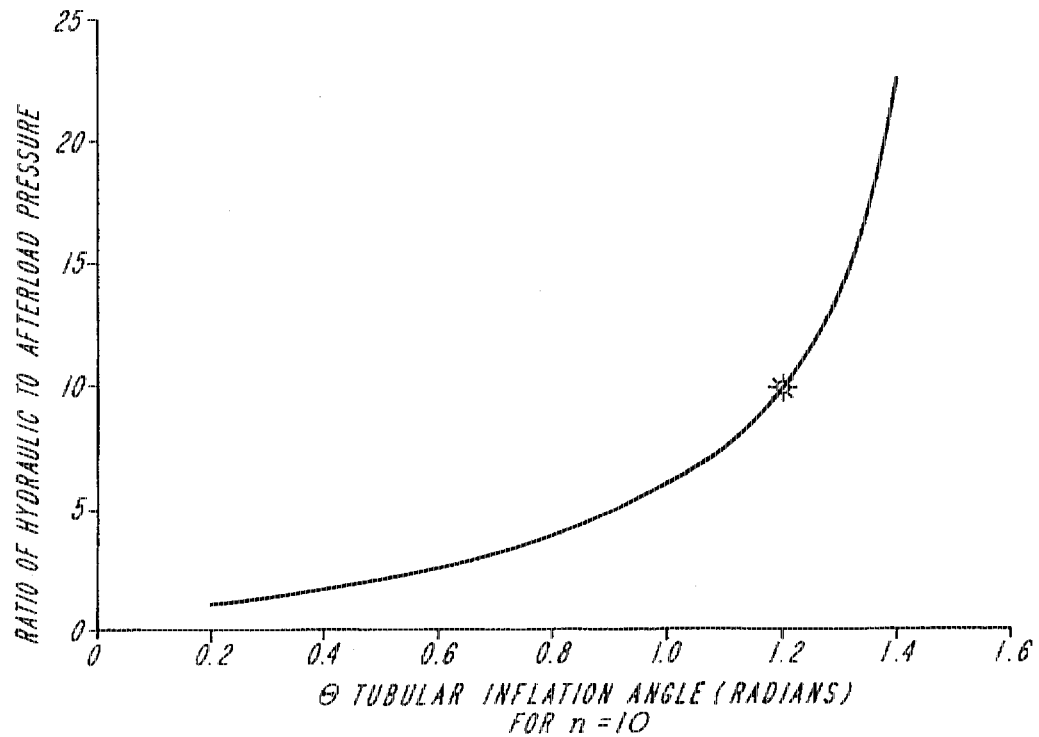
FIG. 7 is a graphical representation of the ratio of hydraulic to afterload pressure as a function of the tube inflation parameter, $\theta$; for n=10.

Illustrated in FIG. 7 is the ratio of the hydraulic to the afterload pressure as a function of the parameter of tube inflation angle $\theta$ for n=10. In the curve of FIG. 7, the targeted operating point is shown by the asterisk. As can be seen a significant contraction is achieved when $\theta$ is between 1.2 to 1.4 radians, representing a 22% to 30% contraction. Thus, the operational range of the hydraulic pressure is near one atmosphere for full assist against an afterload pressure of approximately 90 mm Hg, and ¼ atmosphere for cardiac boosting, that is, increasing the ventricular pressure by 20 to 30 mm Hg.

As discussed earlier the artificial myocardium requires synchronization of its contraction with the natural heart. Contraction of the device must be timed appropriately with the heart's systole. Additionally, the drive pressures during systolic ejection must be maintained to match the needs of physiologic afterloads.

The first factor, that is, the timing, can be achieved by implanting an epicardial lead in a myocardial region of the natural heart not in contact with the artificial myocardium, which could be near the apical region, or at the right atrial appendage. The artificial myocardium would be timed to contract with the R wave produced on this lead. This detection can employ hardware that is used at the present time in implantable defibrillators. The systolic duration (in milliseconds) is preprogrammed to match its functional dependence to the beat rate (BR) in beats per minute expressed as $\tau_S$=549 msec–2×BR.

Figure 8:
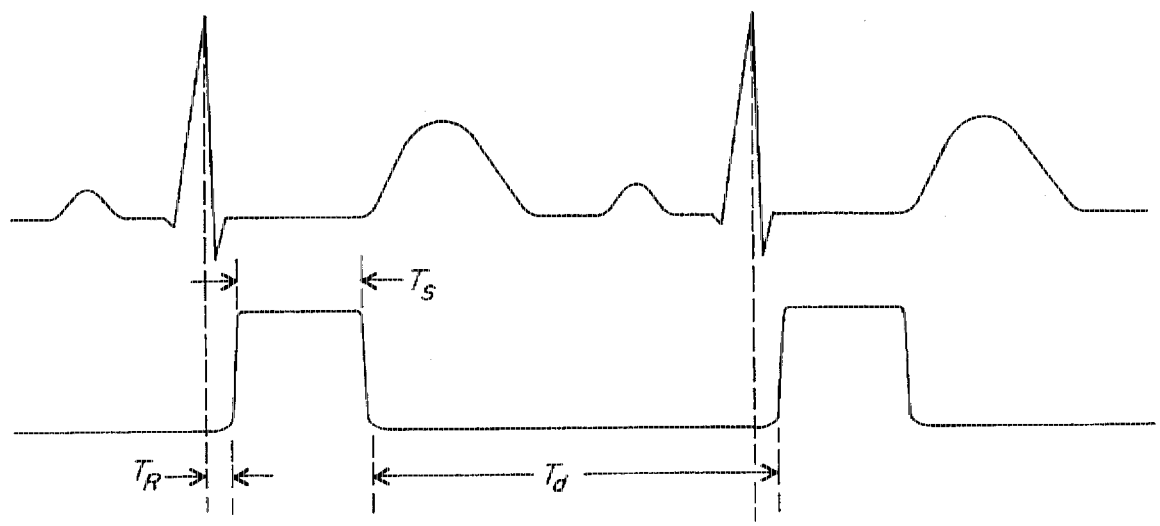
FIG. 8 is a graphical representation of the timing relationship for device actuation.

In FIG. 8 the timing relationship between the ECG and the artificial myocardium is represented graphically. $\tau_R$ is the delay time between the start of the artificial myocardium systole relative to the R wave. $\tau_S$ is the artificial myocardium systolic duration, and $\tau_d$ is its diastolic duration. The exact coincidence of the start of the diastolic duration and the ECG T-wave is not critical. Large deviations from this coincidence could either provide insufficient support ($\tau_d$ starts too early) or hamper diastolic filling (($\tau_d$ starts too late). Of course, irregular rhythms in the natural heart, such as the occurrence of bigeminy, premature ventricular contractions (PVC), or transient arrhythmias can also affect performance of the artificial myocardium system. The most straightforward way of dealing with this situation is to cause the artificial myocardium wrap to be immediately deflated to assume the diastolic state when this occurs. It can also be arranged so that when no ECG trace is detected, the device would contract at beat rates consistent with maintaining physiologic filling pressures. Thus in the extra-cardiac support system of this invention certain unique operating characteristics can be provided when working in conjunction with the natural heart. It can, for example, provide extra contractility not present in other support approaches.

Figure 9:
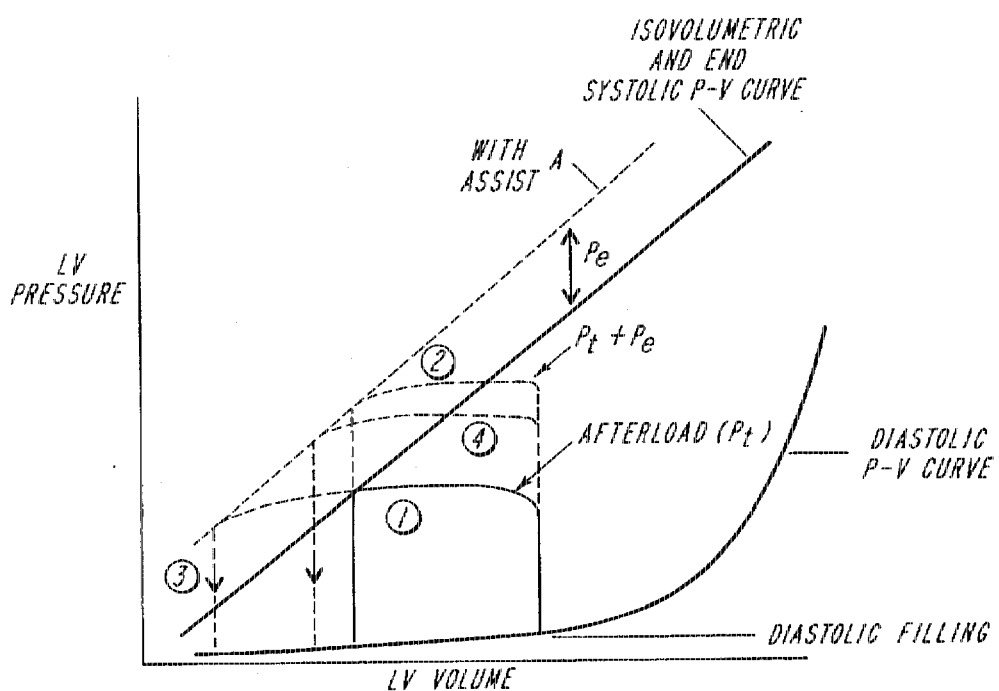
FIG. 9 is a graphical representation of the left ventricular pressure versus the left ventricular volume under various conditions.

FIG. 9 illustrates the left ventricular pressure/volume relationship. In FIG. 9 the left ventricular pressure is plotted against the left ventricular volume. The solid curve (loop 1) illustrates the performance of the natural heart, while the dotted curves show how the pressure volume relationship may be altered in the presence of the extra cardiac assist device. There are two factors which change as a result of the support device: the systolic pressure and the stroke volume. The optimal assist mechanism for this device is to boost the systolic pressure while allowing the myocardium to retain its isovolumetric characteristics by elevating the epicardial pressure ($P_e$) and increasing transmyocardial pressure ($P_t$). The net effect is to displace the isovolumetric curve upwards by $P_e$. This is illustrated by the dashed line A shown in FIG. 9. Whether the intraventricular pressure ($P_V$) remains at $P_t$, achieves the maximum value of $P_t+P_e$, or more likely reaches somewhere in between the two extremes, depends on the vascular resistance and the ventricular stroke volume. FIG. 9 illustrates the three possibilities. In loop 2, the elevated ventricular pressure is matched by an increase in the afterload. This results in no change in stroke volume. In loop 3, the afterload remains unchanged, while the stroke volume is increased by the assist device. Case 2 would result if the ventricular stroke volume is equal to or greater than that available from the device. This represents, nominally, a healthy heart which requires no assist. The control scheme will be based on achieving a full systolic contraction even though the diastolic ventricular filling may not be complete on a beat by beat basis.

With this control scheme, for a healthy heart which can generate sufficient tension against physiologic afterloads, the contractility required of the artificial myocardium would be zero, and minimal hydraulic power would be required to fill the tubes. This in turn generates minimal epicardial pressures and the assist is at a minimum. However, in cases where the natural heart is not capable of generating normal ejection fractions, the device contraction will extend the stroke volume of the ventricle. In order to realize these higher stroke volumes from the ventricle, the artificial myocardium must provide the additional contractility needed. This requires higher hydraulic power resulting in higher epicardial pressure translating to higher ventricular pressure. Under such circumstances, assist will increase flow and the afterload will also increase as a result of the increased flow. This is illustrated by curve 4, the most likely operating P-V loop under assist conditions.

The control scheme is relatively straightforward. The device will be operating at a full systolic stroke in every beat. Power required to achieve the full stroke will be adjusted on a beat by beat basis. The hydraulic stroke volume will be measured on every beat in order to permit implementation of this algorithm. During diastole, hydraulic pressure will be measured to provide an indication of the end diastolic pressures. This information will be used to determine system beat rate for a heart with no rhythm.

Figure 10:
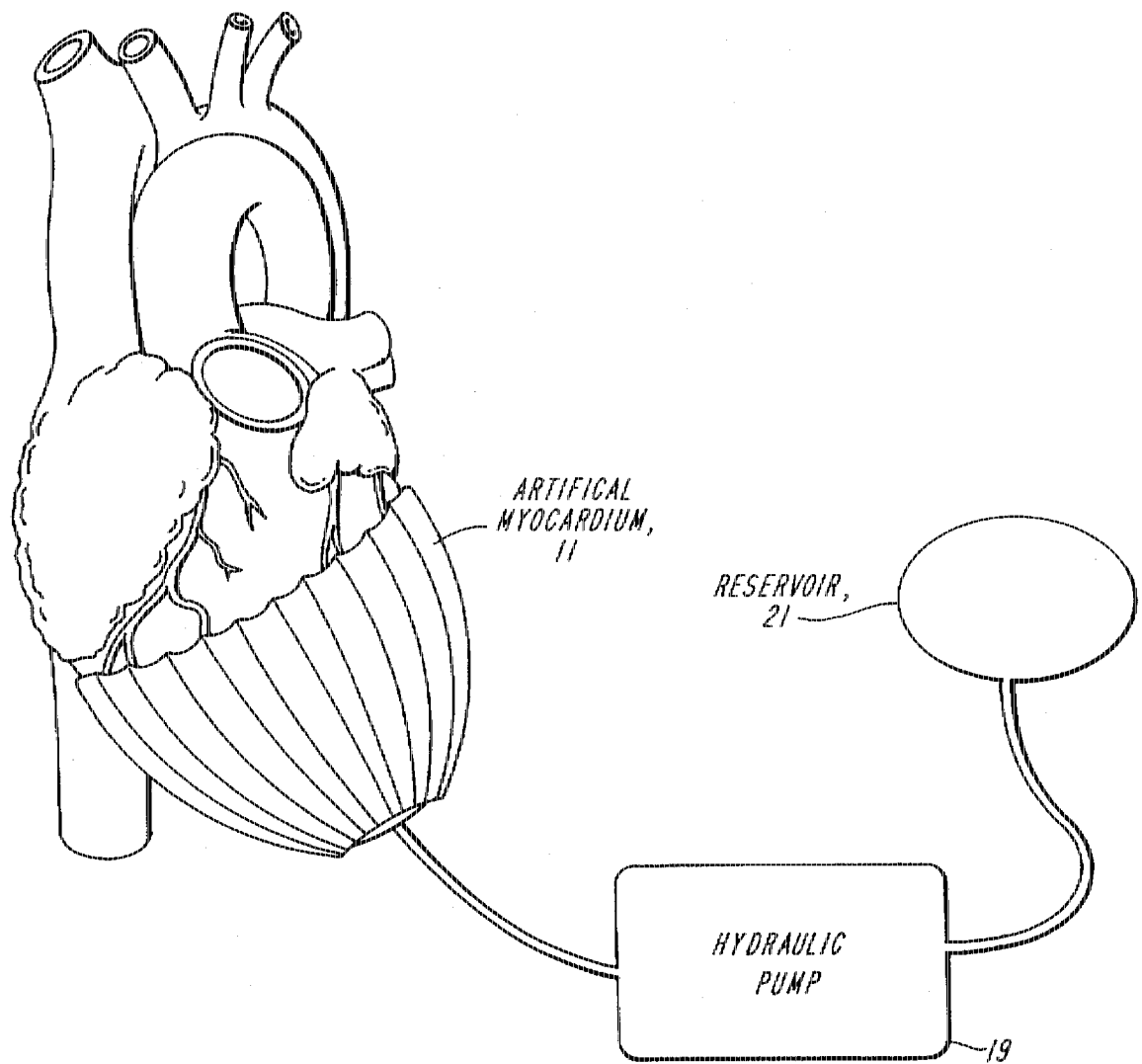
FIG. 10 is a block diagram of the hydraulic system of the artificial myocardium of this invention.

FIG. 10 illustrates in block diagrammatic form the hydraulic system including the artificial myocardium 11, the energy converter 19 and the hydraulic reservoir 21. In one embodiment, the artificial myocardium 11 consists of four layers of polyetherurethane (Angioflex®) reinforced by a polyester mesh, fabricated from 40 micrometer fibers. Two layers of the fiber are interwoven to yield tubular interconnections. Separators are inserted in the individual tubes to prevent the opposing inner walls from bonding with each other during the manufacturing process. The process yields a device which has an overall wall thickness of approximately ½ mm and a strength of 150 lbs/in, nearly two orders of magnitude higher than the tensile forces experienced by the device. Attached to the epicardium of the natural heart, the device, when deflated, represents no additional diastolic resistance to the heart. The energy converter 19 shuttles fluid between the flexible reservoir 21 and the artificial myocardium 11. Fluid reversal is achieved by a rotating valve. The system flow resistance is designed to be low such that in the event of a stoppage of the system, fluid in the tubes of the artificial myocardium will automatically empty into the reservoir 21 within a few heart beats. The positive diastolic filling pressure of the natural hem and the negative intrathoracic pressure insures a driving force to empty the fluid from the device. Once it is completely emptied the artificial myocardium becomes a highly flexible sheet which follows the wall motion of the natural hem without any additional resistance. Such a device can be restarted without any fear of embolic complications after a temporary stoppage.

The direction of hydraulic fluid flow during systole in this cardiac assist device is from the compliant fluid reservoir, through the distributing manifold, and into the individual tubules of the artificial myocardium. During diastole these bladders must be emptied by reversing the direction of hydraulic fluid flow and pumping fluid back into the reservoir. The direction of fluid movement will be reversed by a rotary porting valve in conjunction with unidirectional operation of the centrifugal pump itself.

Unidirectional pump operation has several advantages over reversing the pump direction. Principally, unidirectional rotation of the pump shaft presents much more favorable conditions for bearing life. Although unidirectional pump speed will most likely change between systole (artificial muscle inflation) and diastole, these accelerations and deceleration represents a fraction of those that would be associated with complete reversal of pump direction. Furthermore, in a unidirectional mode, pump impeller design can be optimized for fluid motion in one direction.

Some of the key dimensions and motor performance parameters for a suitable motor for this system are listed below:

overall diameter: OD=1.0 in.
overall length: OL=0.5 in
torque constant: $K_T$=0.4 oz-in/amp
voltage constant: $K_B$=0.3 V/kRPM
terminal resistance: $R_M$=0.325 ohms
viscous damping: FI=0.002 oz-in/kRPM The motor performance parameters listed above were used to predict the anticipated torque-speed and efficiency characteristics of the motor. The torque-speed performance characteristics indicate that the specific operating point of 1.2 oz-in at 35000 RPM can be obtained with an applied voltage of 12 V. In this application, the supply voltage will be larger than 12 V, therefore pulse width modulation (PWM) of the motor supply can and will be used to control speed.

Unidirectional pump operation implies that fluid flow reversal will be accomplished using a rotary porting valve. As illustrated in FIGS. 11A and 11B, a balanced inflow and outflow porting configuration is designed to minimize radial loads. The rotary porting valve 32 consists of two concentric sleeves 34a and 34b, a fixed inner sleeve (not shown) and an outer sleeve 34a which can be rotated through a defined angle by a torque motor (not shown). The valve is composed of two pairs of inlet ports leading to the impeller intake, one pair 40 coming from the fluid reservoir and the other pair 38 from the hydraulic cuff 11, and two corresponding pairs of outlet ports off the impeller, one leading to the distributing manifold and one to the fluid reservoir. Accordingly, the valve is designed so that switching the outer sleeve into the systolic position opens the inlet port from the reservoir while closing that from the manifold, and opens the outlet port to the manifold while closing that to the reservoir. Conversely, switching the outer sleeve back reverses the inlet and outlet ports and generates diastole. The rotary porting valve also incorporates hydraulic dampers to prevent valve rebound at the end of switching. FIGS. 11A and 11B illustrate this valving scheme.

The pump motor bearing is a component which requires careful design considerations By the choice of a unidirectional pump, the major failure mode of bearings due to pump reversals inherent in some designs has been eliminated. However, the artificial myocardium operates at a high RPM in the range of 5,000 to 35,000 RPM. This high RPM places a stringent requirement on the motor bearings.

Bearing load reduction can be achieved by judicious design. Although the outflow pressure is high in the AMA, the surface areas of the energy converter housing exposed to the pressure difference is relatively small, such that the load on the bearings generally remains in the same range. The use of a symmetric paired porting design for the inflow and outflow orifices, allows the radial loads to be reduced to zero.

For any extra cardiac support device, a volume compensating chamber for the actuating volume is required. Since both the left and right sides are not completely independent of the other, the extra cardiac support cannot alternatively pump the left and the right side. In general, for extra cardiac support, the two sides have to be pumped simultaneously. The artificial myocardium inherently has a volume reduction factor requiring only 25 cc of the hydraulic stroke volume for a biventricular support. This compensating chamber can be directly incorporated on the energy converter as a flexing member or it can be separated from the energy converter via a hydraulic conduit and shaped as a pancake flexible chamber. The latter is the preferred approach since this provides additional flexibility in chamber placement. This chamber would be a 2½" diameter sac with flexible membranes to yield a 1 cm excursion. The body of the chamber can be made from Angioflex. A velour layer can be the enclosure to provide tissue layer stability.

The control of the proposed artificial device needs to incorporate three key modes. These are, (1) synchronized contraction and dilatation with the heart when a normal R-wave is discerned, (2) no pumping during intermittent arrhythmia, and (3) pumping at rates determined only by filling pressures during fibrillation and cardiac arrest. An additional design criterion is to ensure that the device does not work against the heart. The proposed control algorithm consists of three modes discussed below.

Synchronization is achieved by sensing the rhythm of the natural heart, or paced signals for subjects with implantable pacers. Two basic approaches are available, using either the P-wave or the R-wave, the choice being governed by the conduction capability of the heart.

P-wave may be preferable as the reference for synchronization, since the right atrium remains free from any mechanical contact with the device. Naturally, if a subject suffers from frequent atrial flutter or atrial fibrillation, reliable P-waves would not be available. In addition, AV block would exclude the use of the P-wave. Patients with these pathologic conditions would require R-wave sensing. Epicardial leads can be used for either sensing mode. For atrial sensing, a lead can be sutured to the atrial appendage, while ventricular sensing can be achieved by a corkscrew electrode attached near the apex where no direct squeezing of the myocardium would occur. Bipolar electrode designs may be used in order to localize signal reception especially, P-waves, with reduced noise pick-up in the acquired signals. Unipolar leads can be used for R-wave sensing since this is the simplest type of electrode for ventricular epicardial fixation.

Whether P-wave or R-wave sensing is used, the algorithm is designed for synchronous contraction of the artificial device and the myocardium. For a subject with a regular heart beat, this can be achieved readily. For P-wave sensing, the device systole is timed to initiate after ~160 msec, a normal AV delay, following P-wave detection. With R-wave detection, device actuation is initiated immediately. An anticipation algorithm which is based on the prior R—R intervals can also be used. Such algorithms are available.

Figure 12B:
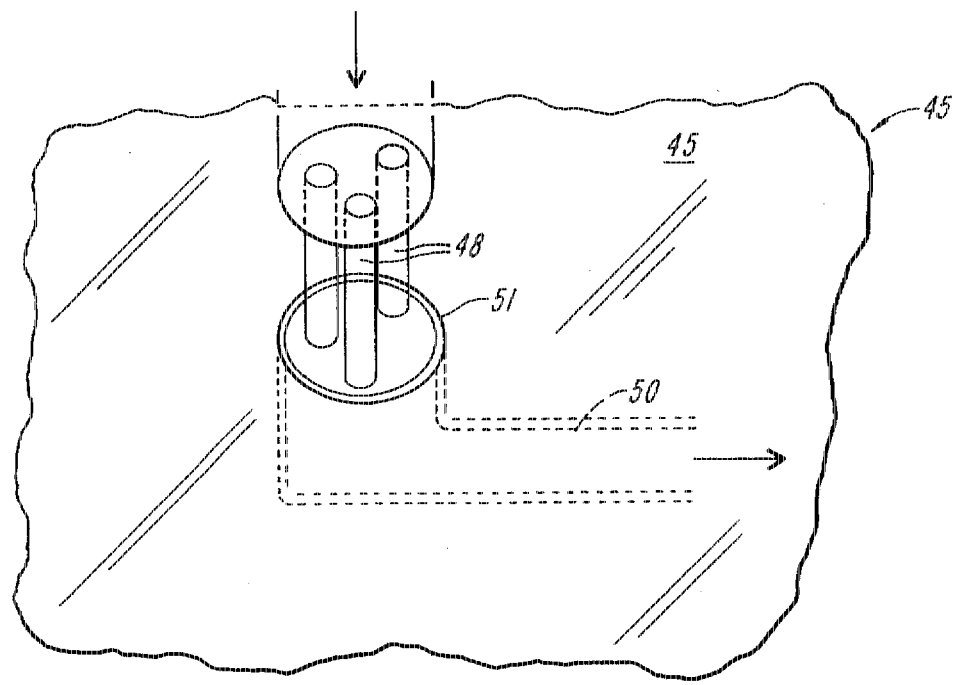
FIG. 12B is an "X-ray" view of the access system of FIG. 12A viewed externally.

In FIG. 12A and 12B there is illustrated a subdermal port for the artificial myocardium assist system in case there is a failure of the hydraulic pumping capacity. FIG. 12A is a cross sectional view across the skin interface 45 and FIG. 12B is an "x-ray" view of the system viewed externally. In the case of a system failure, as a result of electronic or mechanical problems, the subdermal port can be accessed through a skin puncture with an array 48 of 15 gauge needles. The procedure would involve the extraction of the hydraulic fluid using a 50 cc syringe. This extraction would collapse the artificial myocardium cuff 11. A hand operated pneumatic pump (not shown) could then be connected to the needle manifold 47 to activate the artificial myocardium. The reason for the extraction of the hydraulic fluid and subsequent manual use of a pneumatic pump is that the flow resistance through a i cm long parallel array of 15 gauge (1 mm ID) needles is less than 20 mm Hg for air, while the use of hydraulic fluid would result in pressure losses which are orders of magnitude higher. The artificial myocardium system would be implanted through a median sternotomy. This procedure is sufficiently simple so that it would be possible without bypasses, although severely compromised patients might require bypass for support during the surgical procedure. Of course, other, perhaps less invasive, surgical techniques could possibly be employed for this implantation. An appropriately sized artificial myocardium cuff 11 would be wrapped around the natural heart. The energy converter 19 and the hydraulic reservoir 21 would be implanted in the thorax. It is estimated that the total volume and weight of the thoracic unit would be approximately 105 cc and 165 g respectively. The energy converter and the fluid reservoir, which in practice could be an integral part of the energy converter, would be anchored to the rib cage with a flexible hydraulic connection to the artificial myocardium cuff 11 and an electrical cable tunneled through the costal diaphragmatic region to the electronic components which could be implanted in the abdomen. These implant locations are illustrated in FIG. 2. It is important that the artificial myocardium cuff 11 is anchored properly relative to the natural heart such that during systolic contraction, the heart would not slip out of the myocardium cuff 11. Suitable attachment arrangements are, for example, illustrated in U.S. Pat. No. 4,957,477.

The primary biocompatibility issue for the artificial myocardium relates to the epicardial tissue/cuff interface, or pericardial tissue/cuff interface. The material in contact with the epicardium or the pericardium will be the polyetherurethane material Angioflex®. Other implanted components would consist primarily of cable jackets made from either medical grade room temperature vulcanizing rubber (RTV) or Angioflex® polyurethane. Non-flexing parts would consist of titanium as casing for the energy converter and electronics packages. Infectious risks would be minimized in this design by the elimination of percutaneous exit and entry sites into the body, by quality control of surfaces and by choices of materials in contact with the tissue.

Figure 13:
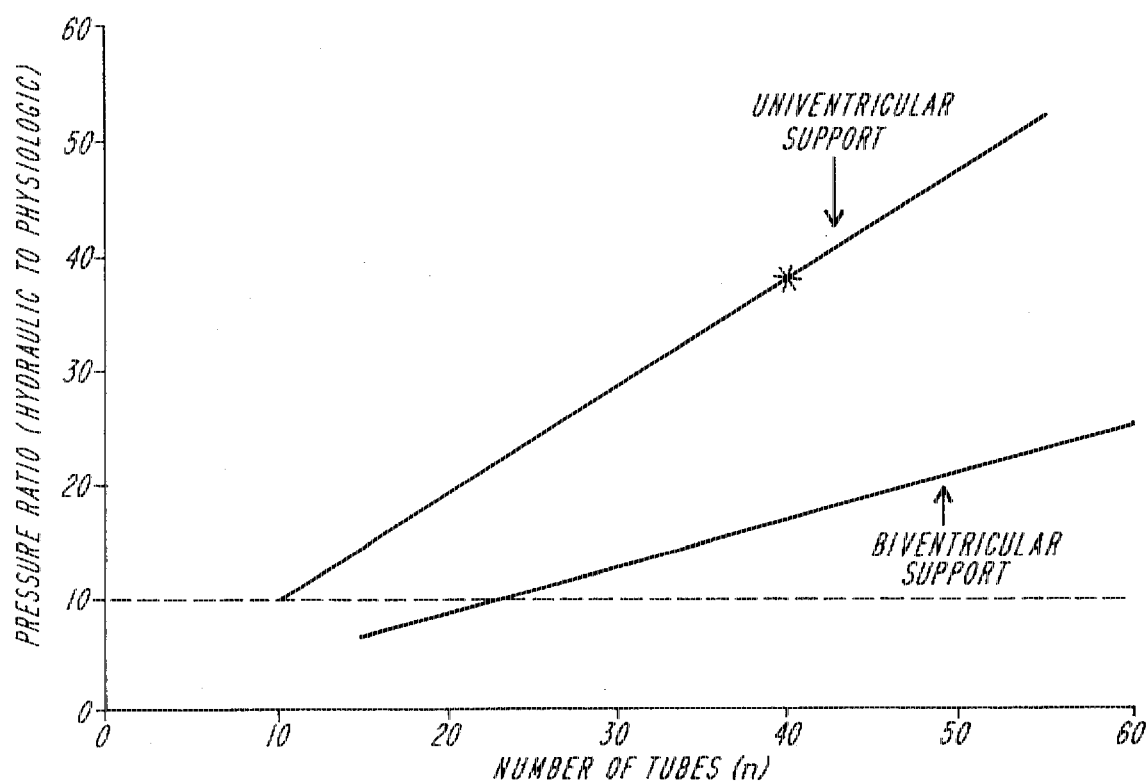
FIG. 13 is a graphical representation of the hydraulic to physiological pressure ratios as a function of the number of tubes for both univentricular and biventricular support.
Figure 14:
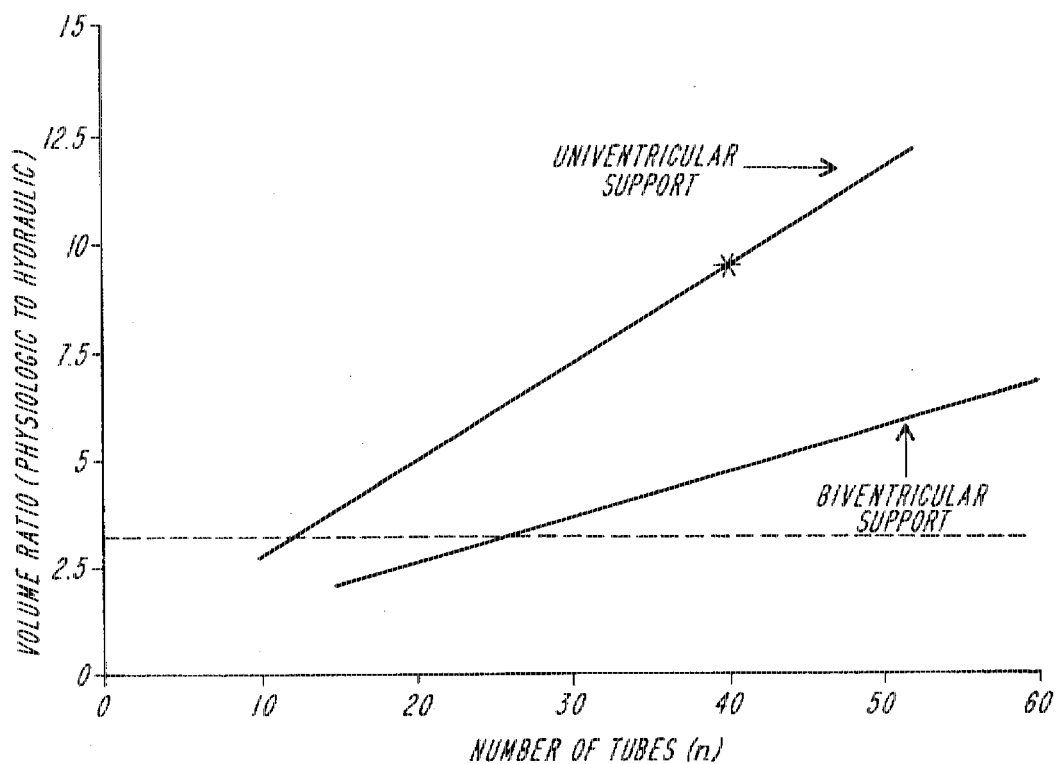
FIG. 14 is a graphical representation of the physiological to hydraulic volume ratios as a function of the number of tubes for both univentricular and biventricular support.
Figure 15:
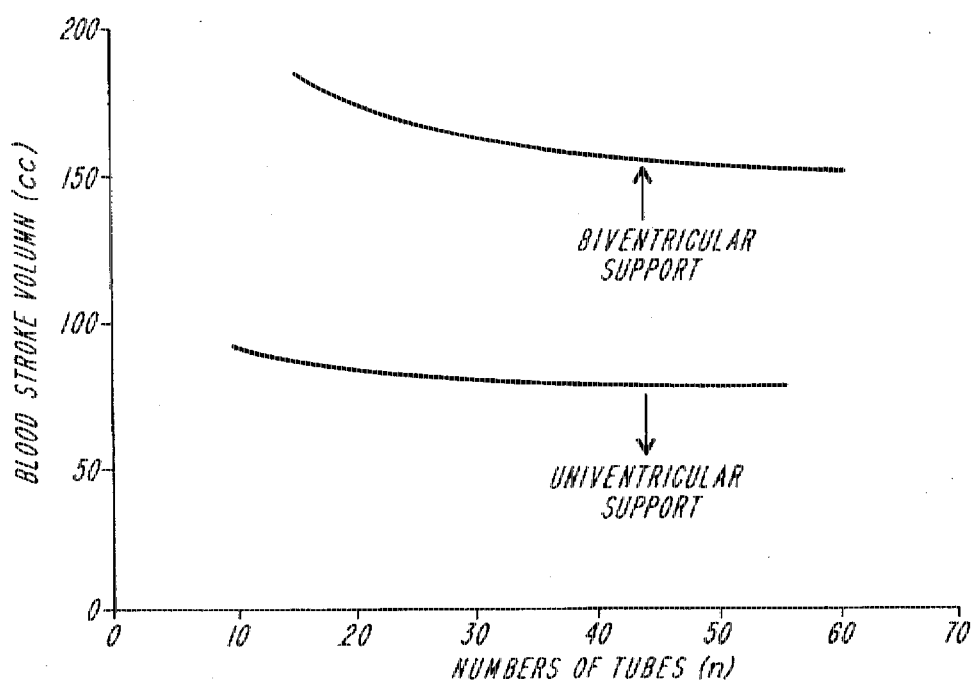
FIG. 15 is a graphical representation of the blood stroke volume as a function of the number of tube segments in the artificial myocardium of this invention.

FIGS. 13 and 14 show the calculated pressure and volume ratios of the hydraulic and physiologic blood system fluids as a function of the number of tubes in the artificial myocardium. FIG. 13 shows the hydraulic physiological pressure ratio as a function of the number of tubes for both biventricular support and univentricular support. FIG. 14 shows the physiological to hydraulic volume ratio. These figures show that as the number of tubular segments increases, the required hydraulic stroke volume decreases while the required hydraulic pressure increases. For a volume ratio of three, the univentricular support (½ of the total wrap) would require 11 segments, while the biventricular support would need 23 segments because of the larger perimeter for biventricular support. This volume amplification between the hydraulic stroke volume and the blood stroke volume is very significant, since it permits the actuating system for the artificial myocardium to be small and compact in size. In order to take advantage of this volume amplification, the pressure required to inflate the tubes to the appropriate extent for a significant stroke work is approximately 10 times the afterload pressure of the blood being pumped. In the figures, the intersections of the univentricular and bioventricular supports with the dashed horizontal line indicate these operating points. FIG. 15 illustrates the blood stroke volume in cc's as a function of the number of tube segments (n) in the artificial myocardium. As illustrated, the stroke volume does not have a strong dependence on n, especially when n becomes large and the hydraulic displacement component becomes negligible compared with the contractile effect. For a completely failed ventricle, in order to generate 100 mm Hg of systolic pressure, the hydraulic drive pressure required will be approximately 1,000 mm Hg. This value is illustrated by the star shown in FIG. 7. The benefits derived from operating the energy converter 19 at lower flow and higher pressures are higher system efficiency as a result of lower flow losses and smaller system size due to the lower volume requirement. The gain in the hydraulic efficiency will be primarily in the energy converter 19. For artificial myocardium cuff 11, the flow velocities in the individual tubes is independent of the number of tubes. The volume of each tube scales with the area of the tube so that the flow velocity is a parameter determined only by physiologic requirements. For a 65 cc stroke volume at a beat rate of 140, the peak hydraulic flow velocity in the tubes is approximately 15 cm per second, resulting in a dynamic pressure of approximately 0.1 mm Hg, which has no impact on efficiency when compared to driving pressures on the order of one atmosphere. With this design, the wall stresses in the artificial myocardium cuff 11 are, as in flow losses, independent of the number of tubes used in the wrap. The wall stresses in the walls connecting the tubes are only functions of the physiological parameters, such as the heart diameter and the physiological pressure. The wall stress is given as the product of the hydraulic pressure $P_H$ and the tube radius, r, and is a constant, independent of the number of tubes, n.

The design consideration for the number of tubes per wrap will be determined by practical considerations such as the fabrication techniques and energy converter efficiency.

Figure 16:
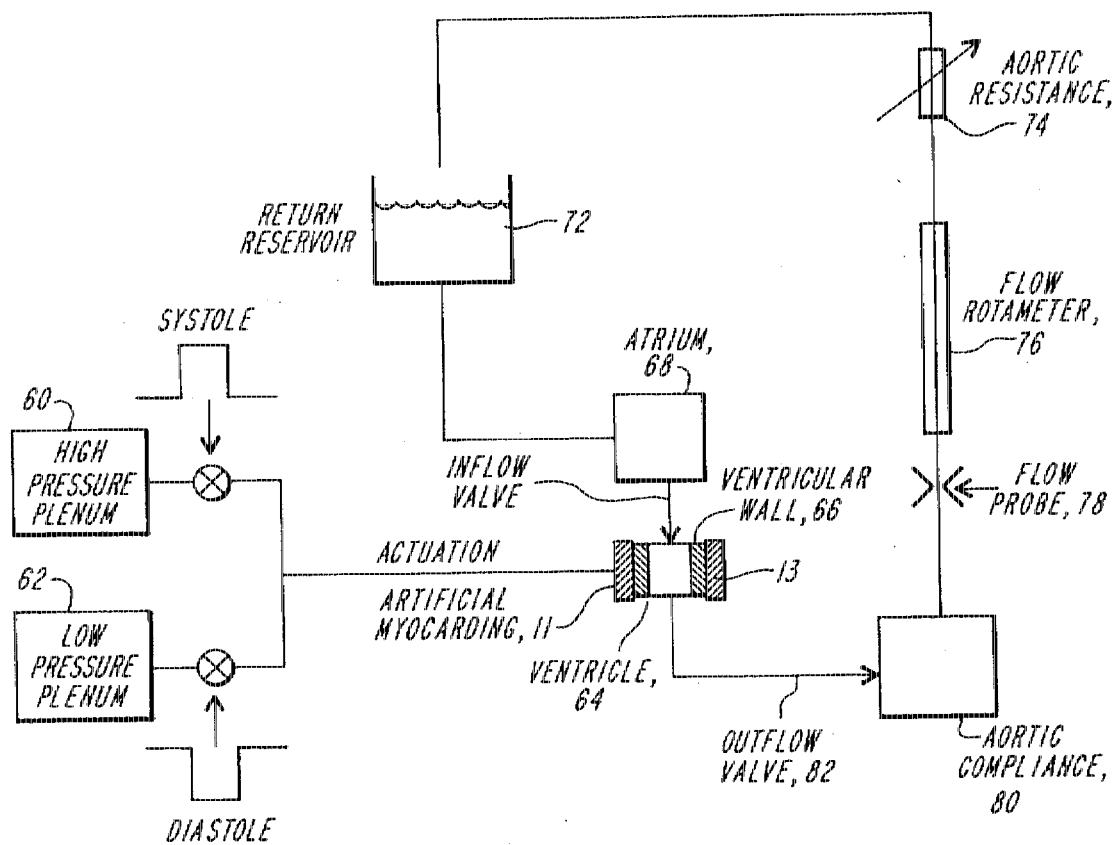
FIG. 16 is a diagrammatic illustration of a mock loop used for in vitro tests.
Figure 17:
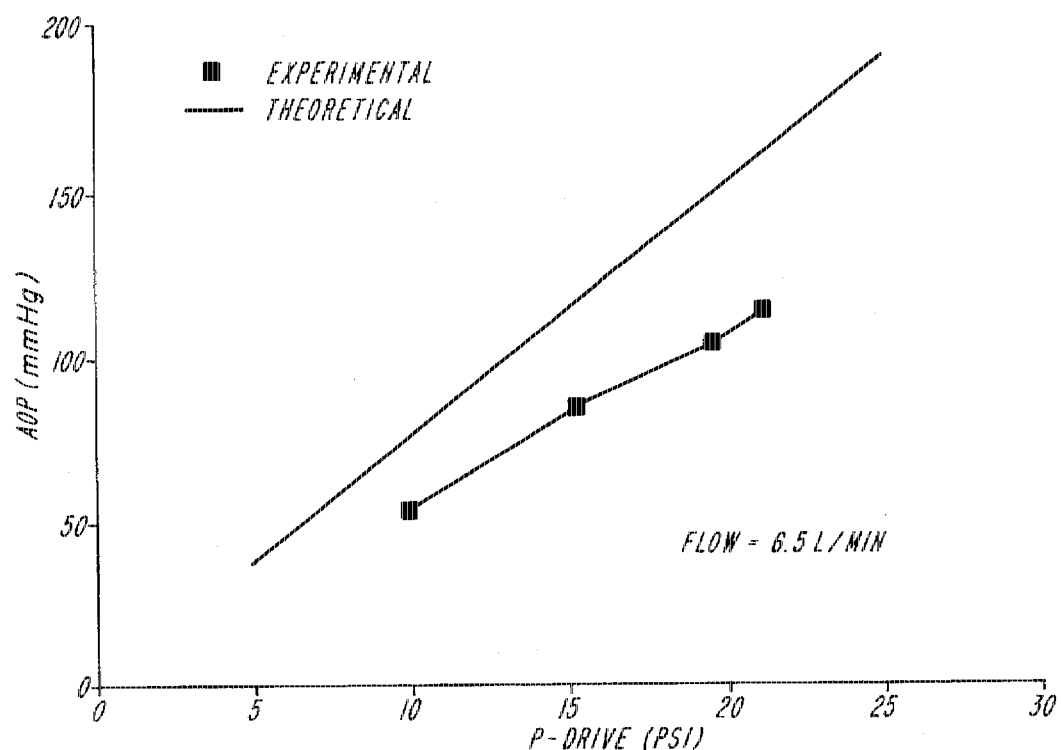
FIG. 17 is a graphical representation of the relationship between Afterload Pressure (AOP) and Driving Pressures (P-Drive) for the artificial myocardium.

FIG. 16 shows a mock loop used for in vitro tests of the artificial myocardium. Fluid from the reservoir 72 enters an atrium 68 which empties through a inflow valve 70 to the ventricle 64. The ventricle consists of a cylindrical bladder which is surrounded by another concentric cylindrical pouch. A space between the bladder and the pouch is filled with a viscous fluid to simulate the ventricular wall. The exterior of the pouch has fitted eyelets spaced to accept an artificial myocardium simulating a left ventricular wrap. The outflow from the artificial ventricle 64 is coupled through another tri-leaflet valve 82 to an aortic compliance chamber 80, followed by a flow probe 78 and a flow rotameter 76. The outflow resistance 74 is adjustable. The return flow empties into the reservoir 72. For this study the artificial myocardium assist system was actuated using a pneumatic drive console consisting of a high pressure plenum and a low pressure plenum which were alternately switched to the device by solenoid valves initiating systole and diastole respectively. This drive mechanism replaces the hydraulic energy converter which would be employed in the implantable system. For this study FIG. 17 illustrates a linear relationship between the afterload pressure (AOP) and driving pressures for the artificial myocardium. The theoretical calculated value is shown as the solid curve, while the square dots indicate the values determined in this experimental study. The flow output was maintained constant by adjusting the aortic resistance. In the illustrated set of measurements the flow was maintained at 6.5 liters per minute, with a filling pressure of 14.6 mm of mercury, a beat rate of 169 beats per minute and a systolic duration and duty factor of 168 milliseconds and 40% respectively. The device used in this study had 7 adjacent tubes and provided 50% wrapping of the pouch simulating the natural heart ventricle. The diameter and length of the pouch were 6 cm and 5 cm respectively, fairly typical of a small, left ventricle. Based on calculations, the anticipated stroke volume was 46.7 cc and the measured stroke volume was 38 cc, 82% of the theoretical value.

Figure 18:
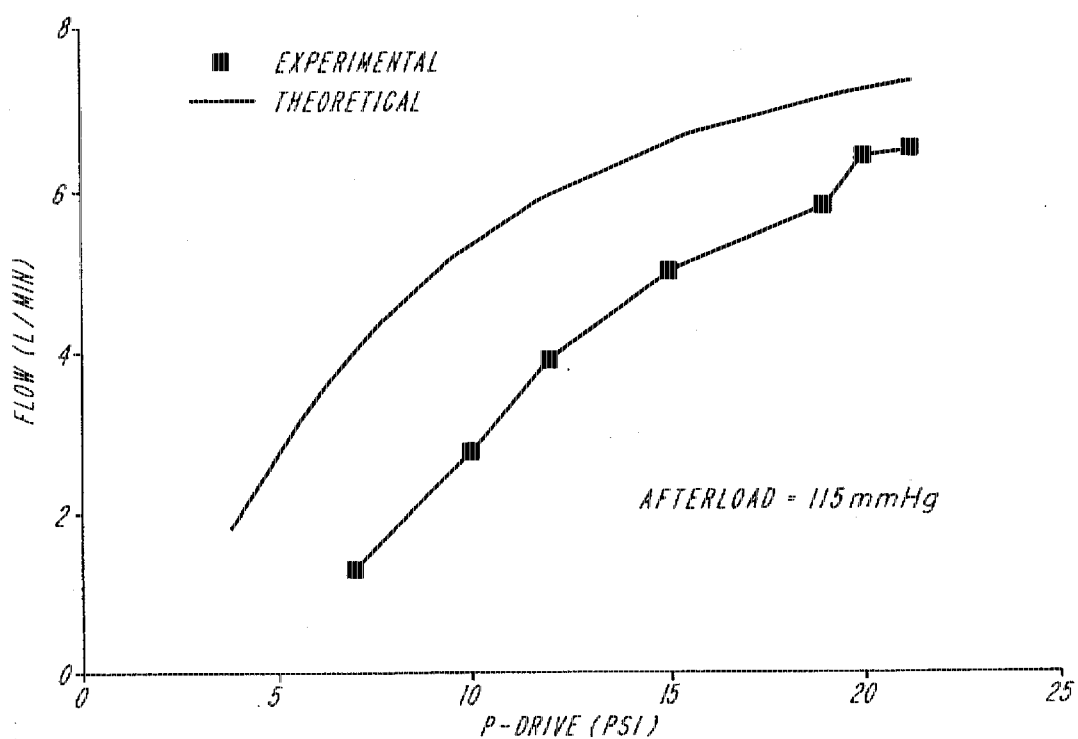
FIG. 18 is a graphical representation of flow sensitivity to drive pressure at a constant afterload pressure.

A second set of measurements was obtained in this study by maintaining a constant afterload, while the drive pressure was varied and the resultant ventricular flow recorded. The results of this study are illustrated in FIG. 18. The solid curve shows the calculated values and the set of square points illustrate the measured values. The conditions were similar to those for the experiment illustrated in FIG. 17. FIG. 18 also illustrates the calculated flow versus the drive pressure relationship. The outflow pressure was set at 115 mm Hg, which is the intercept of the drive pressure at zero flow. This study showed that the experimental pneumatic drive pressure was slightly higher than that which would have been predicted by the theoretical calculation. The data from this study indicates by controlling the drive pressure, which is equivalent to adjusting the contractility of the artificial myocardium, both flow and pressures can be enhanced. While specific details of an artificial myocardium and artificial myocardium assist system have been illustrated, it will be understood that other embodiments may be formed employing the principles of this invention.

We claim:

1. An artificial myocardium for use in a patient as ventricular assist device aiding the operation of a natural heart comprising, an inflatable cuff shaped to conform generally to the shape of a natural heart, implantable within a patient's body, and having open ends, said cuff being formed of an interconnected series of closed tubes formed of a flexible, nondistensable, fluidically sealed material, said tubes being oriented with their long axes parallel to an axis connecting one open end with the other, means implantable within said patient for controllably and periodically filling said tubes with a fluid, such that when filled, each of said tubes assumes a tubular cylindrical shape with a circular cross section, and when emptied of said fluid, each of said tubes assumes a collapsed shape, and control means for providing said periodic sequence of filling and emptying said tubes with said fluid, said control means being adapted to operate in conjunction with the diastolic and systolic pulsing of said natural heart such that said fluid fills said tubes in conjunction with the systolic phase of said natural heart and empties said tubes in conjunction with the diastolic phase of said natural heart.

2. An artificial myocardium in accordance with claim 1 wherein said fluid filling of said tubes is initiated in response to P or R waves produced by said natural heart.

3. An artificial myocardium in accordance with claim 1 wherein the dimension of each of said tubes is selected to contract the volume enclosed by said cuff, when said tubes are filled by fluid, by a length which is substantially 36% of said cuff circumference when said tubes are substantially not filled by said fluid.

4. An artificial myocardium in accordance with claim 1 wherein each of said tubes is formed such that the cylindrical ends of said tubes have a substantially hemispheric shape when said tubes are inflated and wherein said tubes are interconnected along the long axes of said cylinders.

5. An artificial myocardium in accordance with claim 4 wherein the ratio between the inflated length of said cylinders and the diameter of each of said tubes is equal to or greater than about 4.0.

6. Apparatus in accordance with claim 1 and further including, a subdermal access port, implantable beneath the skin of said patient in the chest area, a needle manifold adapted for positioning external to the patient's skin, said needle manifold carrying a plurality of syringe needles for puncturing the skin above said subdermal port, said subdermal port being fluidically coupled to said inflatable cuff to provide for external deflation and inflation of said cuff through said needle manifold in case of failure of said implantable means for controllably filling said closed tubes.

7. An artificial myocardium assist system in accordance with claim 1 wherein said tubes are tapered from one end to the other along their long axes to aid in conforming the cuff shape to that of a natural heart.

8. An artificial myocardium assist system for implanting within a human body for use as a ventricular assist with a natural heart, comprising, an inflatable cuff shaded to conform generally to the shape Of a natural heart and having open ends, said cuff being formed of a interconnected series of closed tubes formed of a flexible, nondistensable, fluidically sealed material, said tubes being oriented with their long axes parallel to an axis connecting the open ends of said cuff, means for controllably filling said tubes periodically with a fluid, such that when filled, each of said tubes assumes a tubular cylindrical shape with a circular cross section, and when emptied of said fluid, each of said tubes assumes a collapsed tubular shape, a fluid reservoir, fluidically connected to said tubes, an electrically energized fluid pump, for pumping fluid within said system between said fluid reservoir and said tubes, a switching means for selectively directing fluid pressure to either said fluid reservoir or to said tubes, a fluid pressure controller responsive to selected electrical impulses from said natural heart to control said switching means to periodically and repetitively fill and empty said tubes, an electrical power source coupled to said electrically energized pump, each of said system elements being formed of a material and structure to be implantable within a human body.

9. An artificial myocardium assist system in accordance with claim 8 and further including a transcutaneous electrical terminal for implantation beneath the skin of a human body and connection to said electric power source.

10. An artificial myocardium assist system in accordance with claim 8 wherein said switching means is arranged to direct said fluid away from said cuff in the event of electrical failure within said system.

11. An artificial myocardium assist system for implanting within a human body for use as a ventricular assist with a natural heart in vivo, comprising, an inflatable cuff formed with open ends, said cuff being formed of a interconnected series of closed tubes formed of a flexible, nondistensable, fluidically sealed material, said tubes being oriented with their long axes parallel to an axis connecting the open ends of said cuff said cuff being constructed for wrapping around at least a portion of said heart, means for controllably, periodically, and repetitively filling said tubes with a fluid, such that when filled, each of said tubes assumes a tubular cylindrical shape with a circular cross section, and when emptied of said fluid, each of said tubes has a collapsed tube shape, a fluid reservoir, an electrically energized fluid pump, for pumping fluid within said system between said fluid reservoir and said inflatable cuff, a switching means for selectively directing fluid pressure to either said fluid reservoir or to said cuff, a fluid pressure controller responsive to selected electrical impulses from said natural heart to control said switching means, an electrical power source coupled to said electrically energized pump, each of said system elements being formed of a material and structure to be implantable within a human body, said cuff when said tubes are inflated with a first volume of hydraulic fluid providing a contraction of the volume enclosed by said cuff substantially in excess of said first volume.

12. An artificial myocardium in accordance with claim 11 wherein each of said tubes is formed such that the cylindrical ends of said tubes have a substantially hemispheric shape when said tubes are inflated and wherein said tubes are interconnected along the long axes of said cylinders.

13. An artificial myocardium assist system in accordance with claim 11 wherein said contraction of said cuff is sufficient when said cuff is wrapped around a natural heart to cause it to eject a blood volume larger than said first volume.

* * * * *